United States Patent [19]

Arai et al.

[11] Patent Number: 4,540,670

[45] Date of Patent: Sep. 10, 1985

[54] METHOD FOR MEASUREMENT OF LIQUID SAMPLES

[75] Inventors: Fuminori Arai; Masao Kitajima, both of Saitama, Japan

[73] Assignee: Fuji Photo Film Co., Ltd., Kanagawa, Japan

[21] Appl. No.: 466,256

[22] Filed: Feb. 14, 1983

[30] Foreign Application Priority Data

Feb. 12, 1982 [JP] Japan .................................. 57-20968

[51] Int. Cl.³ ...................... G01N 21/78; G01N 33/52
[52] U.S. Cl. ...................................... 436/170; 422/56; 435/805
[58] Field of Search ...................... 422/55, 56, 57, 58; 436/169, 170, 174, 179; 435/805

[56] References Cited

U.S. PATENT DOCUMENTS

| 4,050,898 | 9/1977 | Goffe et al. | 422/57 |
| 4,110,079 | 8/1978 | Schaeffer et al. | 422/56 |
| 4,292,272 | 9/1981 | Kitajimae et al. | 422/56 X |
| 4,337,222 | 6/1982 | Kitajima et al. | 422/56 |
| 4,340,565 | 7/1982 | Kitajima et al. | 422/56 |

*Primary Examiner*—Arnold Turk
*Attorney, Agent, or Firm*—Sughrue, Mion, Zinn, Macpeak & Seas

[57] ABSTRACT

In a method for assaying an analyte comprising applying a liquid sample containing an analyte to a spreading layer of a multilayer analysis element comprising a support having laminated thereon at least one reagent layer containing a substrate capable of converting a detectable chemical species upon reaction with the analyte and a liquid sample-spreading layer and then detecting the chemical species, a wetting liquid is applied onto the spreading layer, prior to applying the liquid sample to the spreading layer. A liquid sample having a high analyte content can be measured with high accuracy.

23 Claims, 1 Drawing Figure

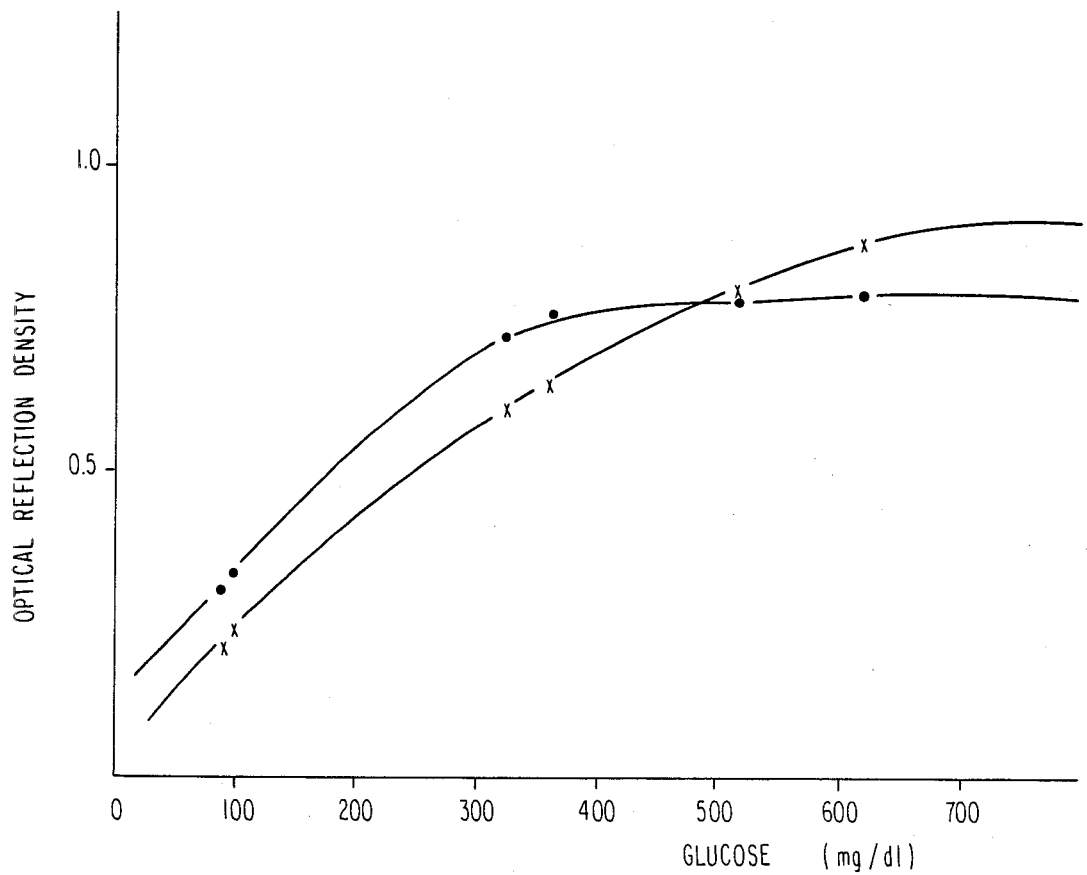

METHOD FOR MEASUREMENT OF LIQUID SAMPLES

BACKGROUND OF THE INVENTION

1. Field of the Invention

The present invention relates to an improved method for quantitative measurement of liquid samples using a dry type procedure (multilayer analysis film technology), more particularly it is concerned with a method for assaying liquid samples especially effective for the quantitative determination of viscous liquid samples such as whole blood that spread poorly when the samples are spotted on the multilayer film.

2. Development of the Invention

Multilayer analysis films are already known which can be used to determine chemical components (especially components that increase the viscosity of the system, e.g., glucose, total protein, triglycerides, etc.) contained in a liquid sample with ease and with high speed via a dry type procedure. For instance, specific examples of such analysis sheets are described in Japanese Patent Application (OPI) No. 53888/74 (corresponding to U.S. Pat. No. 3,992,158), No. 137192/75 (corresponding to U.S. Pat. No. 3,983,005), No. 40191/76 (corresponding to U.S. Pat. No. 4,042,335), No. 3488/77 (corresponding to U.S. Pat. No. 4,006,403), No. 131786/77 (corresponding to U.S. Pat. No. 4,056,898), No. 131089/78 (corresponding to U.S. Pat. No. 4,144,306), No. 29700/79 (corresponding to U.S. Pat. No. 4,166,093) and No. 34298/79 (corresponding to British Pat. No. 2,000,869A) (the term "OPI" as used herein refers to a published unexamined Japanese patent application), U.S. Pat. Nos. 4,110,079 and 4,132,528, *Clinical Chemistry*, vol. 24, pages 1335 to 1350 (1978), and so on.

Such multilayer analysis elements have a common format wherein a spreading layer capable of spreading a liquid sample, layers containing reagents essential to the analysis elements and so on are multi-coated in advance on, a support, and, upon the actual chemical analyses using these sheets, quantitative analysis can be conducted through two basic processes: spotting of the sample liquid into the sheet and evaluation of the extent of dye formation by a specific reaction using a densitometer. These processes are referred to as dry chemical analyses as they do not require processes which are indispensable for conventional methods, such as: arrangement of test tubes; preparation, volume measurement and addition of reagent solutions; accurate weighing-out of samples; and so on.

The basic structure of the multilayer chemical analysis sheet of the type described above comprises a support, a reagent layer and a sample spreading layer, which are arranged in this order.

A liquid drop of a liquid sample dropped onto a spreading layer of the analysis sheet is uniformly diffused over the spreading layer and, at the same time, permeates into a reagent layer, where an analyte contained in the liquid drop is converted into a detectable chemical species (normally color formation or a color change occurs). By observation and quantitative determination of the degree of color formed or the color change, an analyte contained in the liquid sample can be quantitatively assayed.

A major reason for such dry type analysis procedures being operable with good precision is because a liquid sample-spreading layer is arranged to supply a liquid sample to a reagent layer at an approximately constant volume per unit area. Depending upon the volume of the liquid sample applied, this layer acts as a spreader for the liquid sample. In order to obtain a spreading layer having excellent capability for spreading a liquid sample, a variety of materials have recently been studied and developed. In the case of using a liquid sample having high viscosity, especially whole blood or preserved blood having a markedly high hematocrit value as a liquid sample, however, a satisfactory spreading action can be obtained only with difficulty with conventional materials for spreading layers, and regions in which measurement was substantially impossible were present. Taking into account the fact that detection of a disease factor of an abnormally high concentration (also highly viscous) is principally practical in the field of clinical examination, it has been desired that substantially undetectable regions should be minimized as much as possible and the detection range should be broadened as much as possible.

In the prior art, a method in which a highly viscous liquid sample is previously diluted to a suitable region prior to analytical operations (hereafter simply often referred to as "simple dilution") has been adopted. According to this simple dilution method, the degree of dilution can be controlled depending upon the viscosity of a liquid sample so that it must be theoretically possible to measure an analyte utilizing a spreading action of a multilayer analysis film, even though a liquid sample having a high vicosity is employed. However, the level (concentration of color formed or changed) of a detectable signal which is to be formed in a reagent layer is reduced in inverse proportion to the degree of dilution as the degree of dilution of a liquid sample becomes high, and, as a result, there is the danger that optical reading might be inaccurate.

Furthermore, it is difficult to accurately weigh small quantities of a blood sample, particularly having a high hematocrit value and a high viscosity; accordingly, error due to dilution tends to be serious. An error in volume in collecting a sample is particularly serious when small quantities of less than 100 $\mu$l are weighed using a micropipet, etc. Particularly when an amount of a liquid sample is less than several ten times (twenty to fourty) $\mu$l, it is no exaggeration to say that quantitative weighing would be impossible unless a particular device is used and the severest possible attention is paid. Further, in actual dilution, a considerable amount of water must be added to a liquid sample (for example, dilution of a 5 $\mu$l liquid sample using 5 $\mu$l of water is substantially impossible).

In addition, it is required that dilution be carried out outside the reaction system and, as a result, additional processes are added to the measurement procedure. Furthermore, test tubes are required for dilution procedures. Moreover, quantitative determination of an analyte is impossible unless dilution is so accurate that one can determine the degree of dilution. This is because color formed or changed which is actually detected is of the thus diluted liquid sample and the absolute amount cannot be determined unless the degree of dilution is considered. These procedures thus reduce the most advantageous features involved in multilayer analysis films which do not require precise measurement of a definite volume of a liquid sample and permit simple measurement. It has thus been desired to develop a quantitative assay method without impairing these advantages of multilayer analysis films.

One method for improving spreading comprises treating the surface of a liquid sample-spreading layer with a surface active agent, thereby assisting spreading of a liquid sample when the liquid sample is dropped on the spreading layer; such is described in Japanese Patent Application (OPI) No. 131786/77 (U.S. Pat. No. 4,050,898) and No. 164356/80. Further, a method which comprises physically activating a material for a spreading layer by a glow discharge treatment, etc., to thereby assist spreading of a liquid sample is described in Japanese Patent Application No. 140532/80 (OPI No. 66359/82).

In these methods, however, a liquid sample is applied to a multilayer analysis film which is almost completely dried and, as a natural consequence, spreading is not rapidly facilitated since the multilayer analysis film is firstly wetted and then spreading follows. It is known that when surface active agents or highly hygroscopic components such as glycerin or the like are incorporated in a spreading layer, the spreading property is improved; however, the high water content of multilayer analysis materials generally results in the disadvantages of poor reagent stability during storage, undesired color formation (fogging during storage), etc. Thus, in practice there is a limit for imparting hydrophilicity and even in the case that multilayer analysis films having provided the thus improved spreading layer are employed, highly viscous liquid samples that involve disadvantages such as poor spreading, a prolonged period of time for spreading, etc., still exist, and it has been desired to develop multilayer analysis films which can cope with any liquid sample.

SUMMARY OF THE INVENTION

The present invention provides an improved method for measurement which eliminates the foregoing disadvantages involved in the prior art described above.

An object of the present invention is thus to provide an improved method for measurement of an analyte which can broaden the latitude for measurement without impairing the advantages of multilayer analysis films.

A further object of the present invention is to provide a method for measurement in a simple manner in which poor spreading is not encountered even when a highly viscous liquid sample is employed.

BRIEF DESCRIPTION OF THE DRAWING

The FIGURE is a graph showing correlation of glucose content with optical reflection density measured using as a sample preserved whole blood (6 $\mu$l) of various glucose contents. In the FIGURE, x—x indicates the results obtained in accordance with the present invention and ·—· indicates the results obtained per the prior art method.

DETAILED DESCRIPTION OF THE INVENTION

In a method for measurement of an analyte which comprises applying a liquid sample containing the analyte to the spreading layer of a multilayer analysis element comprising a support having provided thereon, in sequence, at least one reagent layer containing a substance capable of converting the analyte to a detectable chemical species, upon reaction with the analyte, through measurements using not only visible rays but also electron rays, UV rays, X-rays, etc., and a liquid sample-spreading layer, and then detecting the detectable chemical species described above, the present invention is characterized in that a wetting liquid is applied to the spreading layer of the multilayer analysis element prior to applying the liquid sample to the multilayer analysis element described above.

The term "detectable chemical species" refers to a detectable signal or change that is directly or indirectly indicative of the presence and/or concentration of a desired analyte, or a reaction or decomposition product of the analyte, e.g., the optical density of a color formed, fluorometric density, electromagnetic (including radiation) intensity or a change in these densities or intensities, etc. For further details, reference may be made to U.S. Pat. No. 3,992,158 and EPC Publication No. 0002963. Preferably, the detectable change that is produced is optically detectable.

The term "liquid sample-spreading layer" refers to a constituent layer having the capability of spreading a liquid sample which meters and distributes a definite volume of an applied liquid sample to a separate reagent layer. Hereafter the liquid sample-spreading layer is often simply referred to as a spreading layer. Details of the function of a spreading layer are described in, e.g., U.S. Pat. No. 4,292,272.

The term "reagent layer" is used to refer to a layer containing at least one component of an interactive composition which, upon interaction with an analyte of the sample liquid, produces or releases a detectable chemical species.

The term "wetting liquid" is used herein to refer to a liquid which is applied onto a spreading layer of a multilayer analysis film and renders the surface and/or interior of the spreading layer wet and to a liquid which is miscible at least with the sample liquid. Accordingly, in the case that the sample liquid is a body fluid such as blood, urine, cerebrospinal fluid, etc., the wetting liquid is a liquid miscible with water. That is, the wetting liquid refers to water or a liquid which can uniformly wet over the spreading layer of a multilayer analysis element and has a low viscosity generally from about 1 to about 50 cps, preferably 1 to 30 cps, measured at 25° C. (hereafter the same).

Representative examples of such wetting liquids include (1) water; (2) glycerin; (3) alcohols (e.g., methanol, ethanol, propanol, etc.); (4) polar solvents (e.g., acetone, tetrahydrofuran, etc.); (5) mixtures of (2), (3) or (4) and water; etc. The mixing ratio of (2), (3) or (4) with water is at least 0.1 vol%, preferably ranges from 1 to 50 vol% and, more preferably ranges from 10 to 50 vol%, based on 100 vol% of water.

Of these wetting liquids, water, glycerin and a mixture thereof (glycerin content, about 10 to about 50 vol%) are particularly preferred.

The term "wetting" is used herein to refer to a state of a spreading layer being uniformly wetted by the wetting liquid described above and in which 0.1 $\mu$l or more preferably 0.1 to 20 $\mu$l, more preferably 0.5 to 20 $\mu$l, of the wetting liquid is contained per 1 cm$^2$ of the spreading layer.

For purposes of improving or accelerating detection reactions (in addition to performing a wetting function), the wetting liquid may contain, in addition to glycerin, a surface active agent, a water-soluble high molecular weight substance such as albumin, etc., water-soluble salts such as sodium chloride, calcium chloride, etc., agents for eliminating interfering substances such as a buffering agent, a bilirubin dissociation agent, a hydrolase, ascorbic acid oxidase, etc.

In the measurement in accordance with the present invention, an analyte is quantitatively determined using a multilayer analysis element (film) comprising a support having multi-coated and/or laminated, in sequence, a reagent layer and a liquid sample-spreading layer in discrete form, where a wetting liquid is firstly applied onto the spreading layer followed by applying a liquid sample thereto. Supply of a wetting liquid onto the spreading layer prior to the application of the liquid sample renders the surface of the spreading layer more wettable and at the same time renders the whole of the spreading layer wettable though a spreading action of the spreading layer. When a liquid sample is dropped onto the spreading layer which has thus been rendered wet, a uniform spreading can be realized in a short period of time even in the case of using a highly viscous liquid sample that undergoes poor spreading per the prior art. The spreading layer per se has the action of uniformly spreading a liquid; however, once uniform spreading of the wetting liquid is effected, the spreading layer is in a state in which the wetting agent is retained. In this case, the physical properties of the spreading layer are not considered to be quite the same as when it is in the dry state. Accordingly, it was assumed that a liquid sample subsequently applied thereto would likewise be uniformly spread. Against this assumption, however, the volume of the liquid sample supplied to the reagent layer is approximately constant per unit area, irrespective of the amount of the liquid sample supplied. Thus, it was found that quite the same function as in the dry state was realized so far as the spreading action of the spreading layer was concerned. It was also found that not only this spreading action was likewise realized even in the case of employing a relatively highly viscous liquid sample but also spreading was effected at an extremely rapid speed as compared to the spreading action of a multilayer analysis film in the dry state to which no wetting liquid is applied. As described above, in the case of previously applying the wetting liquid to the spreading layer prior to the application of a sample liquid, the poor spreading observed in the prior art does not occur.

According to the method of the present invention, a multilayer analysis film is rendered wet at the time of use thereof. The multilayer analysis film is stored in a completely dry state until it is actually employed so that there is no fear of fogging during storage which is considered to be caused by rendering the multilayer analysis film wet.

As described above, it is assumed that the effects of the present invention would be based not only on the fact that the wet state of the spreading layer results from supplying a wetting liquid thereto, but also on the fact that the spreading rate of a liquid sample would be accelerated and, at the same time, a dilution phenomenon as observed in simple dilution would occur microscopically at portions of the spreading layer. This is because when a liquid sample is applied or dropped onto the thus wetted spreading layer, an approximately constant volume of the liquid sample per unit area is supplied to a reagent layer provided beneath the spreading layer in a uniformly diluted state which corresponds to a lower concentration resulting from supplying the wetting liquid. However, such a dilution phenomenon accompanied by the supply of a liquid in a constant volume which occurs in the method of the present invention is quite different from a mere simple dilution. This is supported by the fact that the disadvantage with the simple dilution of the prior art that color density is reduced as a sample liquid is diluted is not observed, rather, a peak in the color density obtained is observed at a certain dilution, depending upon the kind of sample liquid, as will later be described in detail.

The present invention relates to an improved method for assaying a liquid sample using a multilayer analysis element. If conditions are appropriately chosen, it is possible to effect the dilution operation on the spreading layer. Thus, in the case of simple dilution, agitation of a dilution liquid and a sample liquid in any manner is essential to good analytical results, whereas in the present invention, intentional agitation is unnecessary, which is a further characteristic feature of the present invention.

In the present specification, the term "wetting liquid ratio" is used to refer to the ratio of the amount of the wetting liquid to the amount of the sample liquid applied to a multilayer analysis element. Unlike ordinary dilution in which a sample liquid is diluted from 2 times to several ten (20 or 30) times, the wetting liquid used in accordance with the present invention aims at wetting a spreading layer and it is thus preferred that the wetting liquid be employed in the same amount as or less than that of a sample liquid, that is, the wetting liquid ratio be equal to or less than 1. While it is of course within the scope of the invention to use a wetting liquid ratio of 1 or more, the wetting liquid would fill up an area of the multilayer analysis element which is substantially concerned with measurement if the wetting liquid is excessively employed, and, as a result, smooth reaction with an analyte contained in the sample liquid would be prevented.

The wetting liquid employed in accordance with the present invention is not particularly limited as long as it has a viscosity lower than that of a liquid sample applied, does not contain any interfering substance that could lead to an error in measurement of an analyte, and has good compatibility with the liquid sample.

Most typical examples of wetting liquids include water; glycerin, an alcohol, a polar solvent and a mixture thereof with water. In addition, a physiological saline can also be employed. The wetting liquid may further contain salts (e.g., sodium chloride, phosphates, calcium chloride), buffers (combinations of buffers as described in *HANDBOOK OF CHEMISTRY*, Element II, pages 1312 to 1320 (1966), published by Maruzen Publishing Co., Ltd., Tokyo, and *Biochemistry*, 5, 467 (1966), e.g., $Na_2HPO_4$-$KH_2PO_4$, $Na_2HPO_4$-citric acid, tris(hydroxymethyl)aminomethanehydrochloride, etc.), surface active agents (e.g., anionic, cationic and nonionic surface active agents); natural or synthetic high molecular weight substances such as proteins (e.g., albumin); organic or inorganic acids (e.g., citric acid, acetic acid, phosphoric acid, hydrochloric acid, tartaric acid, etc); organic or inorganic alkalis (e.g., sodium hydroxide, sodium carbonate, sodium bicarbonate, ammonia, organic amines such as triethylamine, etc.); oxidation-reduction substances (e.g., ascorbic acid, etc.); or the like. It is preferred that these additions be soluble in water.

The wetting liquid primarily functions to wet a developing layer but, if necessary or desired, it can also serve additional functions. For example, for purposes of further improving analytical accuracy by eliminating and/or inhibiting endogenous competing substances or interfering substances, a variety of additives can also be added to the wetting liquid. The kind of such additives and the actions or functions thereof are widely known in conventional analysis of the wet procedure type but representative examples thereof are given below:

TABLE 1

| Analyte | Additive | Object, Function, etc. |
| --- | --- | --- |
| Urine | pH Buffer Neutralizing Agent | A sample is neutralized to optimal pH since pH widely changes depending on the sample. |
| Sugar | Ascorbic Oxidase | Removal of interfering material (ascorbic acid) |
| | Sodium Azide | Removal of interfering material (catalase) |
| Neutral Fats | Esterase | Diffusion of triglycerides |
| Bilirubin | Cafein Benzoic Acid | Dissociation of protein-binding bilirubin and improvement in spreading bilirubin |
| Cholesterol | Cholesterol esterase Lipase | Improvement in diffusion of cholesterol |
| Components in Whole Blood Plasma or Serum | Protein-removing agent | Removal of proteins |
| Components in Whole Blood or Plasma | Anticoagulant | Prevention of blood coagulation |

In addition, the following additives may also be incorporated into the wetting liquid to improve or assist the function of the wetting liquid as given below:
(1) Surface active agents: Affinity (or wettability) to the spreading layer is increased.
(2) Salts: Permeation of a sample liquid into the spreading layer is improved. The addition of salts is particularly effective for blood used as a sample liquid since blood is maintained under a physiological condition, especially where hemolysis is accompanied by the use of pure water.
(3) Acids or alkalis: Where enzyme activity depends upon the pH of the system, the addition of acids or alkalis accelerates or discontinues an enzyme reaction(s) by controlling pH of the system. For example, in assaying urease for determining the urea content, the sensitivity is reduced when acids are previously added to the system; when alkalis are previously added, ammonia is released to thereby accelerate an enzyme reaction(s).
(4) Oxidation-reduction substances: Side reactions are prevented.

The present invention is concerned with an improvement in multilayer analysis elements which can broaden the latitude of measurement in a simple manner without impairing the advantages of multilayer analysis elements, such as high accuracy. In the present invention intentional agitation of a wetting liquid and a sample liquid is not required. A major object of using a wetting agent is to effect uniform spreading over the surface of a multilayer analysis element. By the uniform spreading action of a spreading layer of a multilayer analysis element, a wetting agent is also uniformly spread. Accordingly, even a wetting liquid need not be accurately weighed if conditions are chosen appropriately. Conditions for wetting a spreading layer with good reproducibility vary depending upon material, structure, layer thickness, surface treatment, etc., for a spreading layer as well as properties of a wetting liquid.

The wetting liquid can be supplied to a spreading layer directly or indirectly, e.g., by directly spotting or dropping onto a spreading layer (e.g., using a micropipet), by means of indirectly supplying a wetting liquid by impregnating a liquid-retaining carrier (e.g., a cotton applicator, a filter-paper stick) with a wetting liquid and then pushing it onto a spreading layer, by means of immersing a paper strip in a wetting liquid to thereby get the stick wet, putting the paper stick on a spreading layer and then pressing, or by means of spraying a wetting liquid onto a spreading layer, etc.

The wetting liquid is applied prior to application of a sample liquid to a spreading layer. It is preferred that the wetting liquid be applied to a spreading layer as close as possible to application of a sample liquid; that is, a sample liquid is applied to a spreading layer immediately after spreading of the wetting liquid. In the case that the amount of the wetting liquid is large, e.g., more than 20 $\mu$l, the timing of the subsequent application of a sample liquid is particularly important. In the case where the wetting liquid is employed in an amount of 5 $\mu$l/cm$^2$, poor results were obtained when 10 seconds or more passed after wetting until a sample liquid was applied, as compared to application immediately after wetting. It is generally preferred that the time period from wetting to subsequent application of a sample liquid be within 30 seconds immediately after the wetting. In the case that the wetting liquid is employed in a small amount e.g., less than 1 $\mu$l/cm$^2$, the time period from wetting to subsequent application of a sample liquid is greatly prolonged. Particularly when an aqueous component which has low volatility, such as glycerin, etc., is contained in a wetting liquid, the time period from wetting to subsequent application of a sample liquid is not overyly important.

The amount of the wetting liquid applied is sufficient as long as the wetting liquid renders at least the surface of a spreading layer of a multilayer analysis film wet. Accordingly, the amount of the wetting liquid is determined depending upon the size and material of a spreading layer but it is generally preferred that the wetting liquid be employed in an amount ranging from about 0.1 $\mu$l/cm$^2$ to about 10 $\mu$l/cm$^2$. In case that the amount of sample liquid applied ranges from 2 to 10 $\mu$l, a particularly preferred amount of the wetting liquid is between 0.5 and 15 $\mu$l and the volume of the ratio of the wetting liquid to the sample liquid (wetting liquid ratio) is between 0.1 and 2, preferably between 0.5 and 1, inclusive. In order to improve poor spreading and at the same time realize dilution and metering effects, it is desired that the whole of a spreading layer be rendered wet.

In the case that a sample liquid contains an analyte at a markedly high concentration or a relatively high viscosity (approximately 20 to 50 cps), a wetting liquid is previously supplied in a predetermined amount onto a spreading layer so as to provide a 1:1 to 0.1:1, preferably 1:1 to 0.5:1, wetting liquid ratio; subsequently a sample liquid is supplied in a predetermined amount, for example, 10 $\mu$l. Then, the sample liquid thus diluted to a desired degree is supplied to a reagent layer beneath the spreading layer in an approximately constant amount per a unit area.

In the case that glucose or cholesterol at a high concentration is detected using an oxidase enzyme, there are optimal conditions for the relationship between wetting liquid ratio and a detectable chemical species produced in a reagent layer, e.g., the color density of a colored substance. According to simple dilution conventionally employed, color density becomes small in inverse proportion to the degree of dilution as the degree of dilution becomes large. To the contrary, such an inversely proportional relation is not observed in the present invention; rather, a peak of color density at a certain wetting liquid ratio is observed.

The degree of dilution showing the maximum color density varies depending upon the kind of detectable species, i.e., kind of an analyte. For example, in measurement of glucose in whole blood, it is observed that a system using 1 volume of whole blood and 1 volume of a wetting liquid (wetting liquid ratio of 1) provides higher color density than a system using 1 volume of whole blood and 0.2 volume of sa wetting liquid (wetting liquid ratio of 0.2). An example will be given hereafter. As described above, if the amount of wetting liquid is small, uniform spreading of a whole blood sample is prevented but dilution alone is effected and poor spreading results so that good color formation is obtained only with difficulty. If the amount of wetting liquid is excessively large, color density is also decreased. This is believed to be because the supply of oxygen required for oxidation of an analyte with an oxidase enzyme is inhibited.

The multilayer analysis element (or film) employed in the method of the present invention is conventional and essentially composed of three layers comprising a support, at least one reagent layer and a spreading layer; a typical construction of the multilayer analysis element (or film) is shown in, e.g., U.S. Pat. No. 4,292,272, which is hereby incorporated by reference.

A thickness of each of those layers is conventional and appropriately chosen by common knowledge in the art. A general guideline is as follows:

| | |
|---|---|
| reagent layer: | 1 to 50 µm |
| spreading layer: | 50 to 500 µm |
| support: | 50 µm to 2 mm |

Turning firstly to the spreading layer, as long as the spreading layer is constructed of materials having the property of spreading a sample liquid, there is no particular limit thereon. As paper for the spreading layer, a wide variety of paper is employed as long as it is water-permeable. For example, filtering paper can be employed and thin, fine filtering paper is particularly preferred. Indian paper; Japanese paper such as Broussonetia kazinoki, Edgeworthia papyrifera, etc., can also be advantageously employed. Not only paper made of natural cellulose but also paper obtained by subjecting synthetic high molecular weight substances to paper-making to thereby obtain a paper-form and impart water-permeability to the same, paper obtained by subjecting a mixture of synthetic high molecular weight substance fibers (pulps) and natural pulps, asbestos and glass fiber-filtering paper can also be employed as the spreading layer.

In more detail, as materials that can be used in the spreading layer, non-fibrous materials such as polymer filtering membranes—which are known membranes for filtering polymers—having a variety of pore sizes, cephadex, agarose, dextran, etc.; natural fibers such as pulp, cotton, silk, wool, etc.; semi-synthetic fibers such as cellulose esters, viscose rayons, etc.; synthetic fibers such as polyamides, polyesters, polyolefins, etc.; fibrous inorganic materials, e.g., glass fibers, colored glass fibers, asbestos formed into a woven cloth, felt or nonwoven cloth shape can be employed.

Typical examples of membrane filters include Microfilter (made by Fuji Photo Film Co., Ltd.), Millipore (made by Millipore Corporation), etc. These membrane filters generally possess a pore diameter of about 0.2 to about 20 µm, preferably 0.3 to 5.0 µm, more preferably 0.5 to 1.2 µm.

A wide variety of fabrics can be employed as the reaction layer, and of various fabric tissues, plain weave, which is formed by weaving warp and weft yarns alternately, is preferably used. As for the warp and weft of the plain weave, a desirable count ranges from 20 to 120. Of fabrics having the tissue form called a plain weave, cotton fabrics of the types named close cloth, canequim, broadcloth and poplin are preferably employed. In addition to other natural fibers woven in the same manner as the above described cotton fabrics (e.g., kapok, flax, hemp, ramie, silk and so on), fabrics obtained by weaving mixed yarns of chemical fiber (e.g., viscose rayon, cupro-ammonium rayon, cellulose acetate, vinylon, polyethylene terephthalate or so on) and cotton fiber in the same manner as in the above described cotton fabrics, and fabrics obtained by weaving chemical fiber yarns in the same manner as in the above described cotton fabrics can also be employed.

It is preferred that the porous material possess voids of about 20 to about 90%, preferably 50 to 90%, while void percentage varies depending upon the kind of the porous material, pore size, etc. The term "void" refers to a ratio of a space per a unit volume 1 $m^3$ and is expressed by percentage.

Porous material having various pore sizes of about 0.2 to about 20 µm can be appropriately chosen depending upon the kind of an analyte. For example, in the case that the analytes are low molecular weight substances such as insulin, drugs, etc. (these have a molecular weight of from about 400 to about 10,000), porous materials having a relatively small pore size are preferably used; if analytes have a relatively high molecular weight such as immunoglobulins (the molecular weight of which is about 160,000) or albumin (the molecular weight of which is about 75,000), porous materials having a relatively large pore size are used.

It is preferred that these fabrics be rendered hydrophilic.

As examples of processes for rendering fabrics hydrophilic, mention may be made of a process in which commercially produced fabrics are washed and rinsed thoroughly with water to remove starch and other processing materials therefrom and optionally they are further dipped with a 1 to 5% aqueous solution of a surface active agent(s); a process in which such a surface active agent(s) is incorporated into a fabric in a proportion of 0.1 to 10% per unit weight of fabric by spraying an aqueous solution of a surface active agent(s) onto the fabric to wet the same and then drying; etc.

In another type of process for rendering fabrics hydrophilic, fabrics are wet with hydrophilic polymer solutions, which may contain a fine powder(s) such as titanium oxide, barium sulfate and the like, and a wetting agent(s) such as glycerin, polyethylene glycol and the like, in addition to hydrophilic polymers such as gelatin, polyvinyl alcohol and the like, and then dried. Hydrophilic polymers are incorporated in fabrics in proportion of from about 0.05 to 10% by weight and preferably from about 0.1 to 5 wt%, per unit weight of fabric. Further details thereon are given in Japanese Patent Application (OPI) No. 164356/80 and U.S. Pat. No. 4,292,272.

Further when finely divided granules such as dextran, agarose, acrylamides, celluloses, etc., are intermixed with these porous materials, especially with fibrous porous materials the, water-retaining property of a sample liquid is improved.

The construction of the spreading layer and materials used therefor are described in, e.g., Japanese Patent Application OPI Nos. 164356/80 and 53888/74 and Japanese Patent Application No. 34370/81.

The spreading layer described about is located as an outermost layer of the multilayer analysis film and has a thickness of from about 50 to about 500 μm, preferably 100 to 200 μm.

The reagent layer used for an analysis element in accordance with the present invention is a layer 1 μm to 100 μm thick of a composition prepared by dispersing a reagent for determining the specific component in a liquid sample in a hydrophilic binder such as gelatin, polyvinyl alcohol, polyvinyl pyrrolidone, agarose, sodium polyvinylbenzenesulfonate, etc. For example, a representative composition for the reagent layer for assaying glucose in a sample liquid comprises glucose oxidase, peroxidase, 4-aminoantipyrine and 1,7-dihydroxynaphthalene. Such a reagent layer for glucose assay is prepared by forming a layer having a thickness of 10 to 20 μm from the foregoing 4 components using gelatin as a binder.

The reagent used for determining an analyte in a liquid sample will be self-evident to one skilled in the art and hence is not explained in detail in this specification.

The spreading layer described above is provided by laminating the foregoing spreading layer on the reagent layer and then adhering these layers to each other or by coating a dispersion of a composition constituting a spreading layer followed by drying.

The reagent layer can be divided into two or more layers. This is because stepwise reactions are sometimes more effective in the case of producing a detectable species utilizing conjugated reactions.

As the support, conventional water-impermeable transparent supports preferably having a thickness of about 50 μm to about 2 mm, such as polyethylene terephthalate films, cellulose esters (cellulose diacetate, cellulose triacetate, cellulose acetate propionate, etc.,) films, polycarbonate films, polymethyl methacrylate films, etc., and glass sheets are conveniently used. Further, as the support, opaque supports such as parting papers, etc., prepared by dispersing a pigment such as carbon black, titanium oxide, phthalocyanine copper, etc., in the aforesaid transparent supports can be used. In this case, after finishing the analysis reaction, the support is peeled off prior to performing measurement.

In addition to the foregoing basic layers, various layers can also be optionally provided for purposes of assisting the structure and/or function of the multilayer analysis element. For example, such additional layers include an adhesion layer for improving adhesion between the basic layers, a color shielding layer or a light reflection layer for assisting measurement, etc.

As materials for an adhesion layer, hydrophilic polymers used for binders of layers for assisting analytical functions such as a color shielding layer, a light reflection layer, etc. can be used. Examples of binders which can be employed in these layers include natural hydrophilic high molecular weight substances such as gelatin, agarose, sodium alginate, carboxymethyl cellulose, methyl cellulose, etc.; hydrophilic synthetic high molecular weight substances such as polyacrylamide, polyvinyl alcohol, polyvinylpyrrolidone, sodium polyacrylate, polyhydroxyethyl methacrylate, copolymers containing acrylic acid (e.g., styrene-acrylic acid copolymer), copolymers containing maleic acid (e.g., maleic anhydride-methyl vinyl ether copolymer), etc. In this case, a liquid sample-spreading layer is put on an adhesion layer in a state where a hydrophilic polymer of the adhesion layer is half-dried or after the hydrophilic polymer is wet with water or with water containing a surface active agent; thereafter these layers are pressed under an appropriate pressure. The thickness of the adhesion layer ranges from 0.5 to 15 μm, preferably 0.5 to 5 μm.

When the method of the present invention is applied to the thus constructed multilayer analysis film, quantitative assay can be performed in a simple manner even with a sample liquid containing an analyte having a high concentration which was impossible to measure per the prior art, or with a sample liquid having high viscosity. According to the method of the present invention, results can be obtained with high accuracy.

Liquid samples which are advantageously applied to the method of the present invention are those having high viscosity (more than 20–23 cps) for some reason, e.g., whole blood, especially preserved blood, blood having a high hematocrit value, blood where coagulation was initiated, blood having high protein content, blood where substances for increasing viscosity are present (for example, blood having a high content of glucose, total protein, triglycerides, etc. ), etc.

Advantages of the present invention are summarized below:

(1) Spreading of a liquid sample is improved or spreading of a liquid sample that was said to be impossible is made possible.

(2) The effects of uniform dilution and metering a liquid sample to a reagent layer are achieved.

(3) A container for dilution is unnecessary.

(4) The method of the present invention can be applied to a sample liquid collected from a patient having exceptionally high concentration of an analyte, without requiring any special equipment and the latitude of measurement is broadened.

(5) A simple operation in a short period of time is sufficient.

(6) Dilution can be effected over a wide range.

Hereinafter, the method of the present invention will be described in detail with reference to the examples below. In the examples, the multilayer analysis slide employed was prepared in a manner similar to Example 2 of Japanese Patent Application OPI No. 164356/80 except that one surface of a mixed spun broadcloth of cotton and polyethylene terephthalate was subjected to a glow discharge treatment and the thus obtained multilayer analysis film was mounted in a slide frame as disclosed in Japanese Utility Model Application OPI No. 142454/81.

EXAMPLE 1

Glucose was added to blood collected from normal human to prepare a sample liquid containing a glucose content of about 650 mg/dl. This sample liquid (6 μl) was dropped on the above described slide for assaying whole blood. After incubation for 6 minutes, measurement was performed at an optical reflection density of 500 nm. The glucose content found was 0.87 g; a color formed was unstable and reproducibility was poor.

Next, prior to dropping of the same sample liquid of whole blood, 10 μl of a saline solution containing 10% glycerine and 20 mM phosphate buffer (pH 7.0) was dropped on the slide and the whole blood sample was dropped thereon 5 seconds after. Subsequent measurement operations were repeated as described above. Optical reflection density at 500 nm was 0.981; uniform color formation was obtained with good reproducibility.

EXAMPLE 2

In place of the glycerin aqueous solution used in Example 1, 10 μl of a 7% aqueous albumin solution was dropped on the spreading layer of the above described multilayer analysis slide. Optical reflection density at 500 nm was 0.968. After repeating the described procedure, good reproducibility was obtained.

EXAMPLE 3

On a spreading layer of the multilayer analysis slide, 10 μl of a wetting liquid consisting of a 10% glycerin aqueous solution containing 0.9% sodium chloride was dropped. Then, the same procedures of dropping and incubation as in Example 1 were performed using preserved whole blood containing various concentrations of glucose, i.e., 100, 200, 300, 400, 500 and 600 mg/dl. Optical reflection densities were measured at 500 nm. The results are shown in the FIG. 1 by the line connected with x marks.

After diluting the thus obtained samples in dilution cells using a wetting liquid having the same composition as described above, the respective samples thus diluted were dropped onto the spreading layer of the multilayer analysis slide. After incubating in the same manner as described above, optical reflection densities were measured, respectively. The results obtained are shown in FIG. 1 by the line connected with dots.

As is seen from FIG. 1, the glucose content becomes high in the case of performing dilution outside the system; when the glucose content exceeds 400 mg/dl, the proportional relation between glucose content and optical reflection density is lost. That is, according to conventional dilution, the results indicate that quantitative assay is impossible with whole blood having a glucose content of 400 mg/dl or more. On the contrary, according to the method of the present invention a good linear relationship was obtained between glucose content and optical reflection density even with whole blood showing a glucose content of 400 mg/dl or more. From this result, it is understood that the range for measurement is broadend in the method of the present invention.

While the invention has been described in detail and with reference to specific embodiments thereof, it will be apparent from one skilled in the art that various changes and modifications can be made therein without departing from the spirit and scope thereof.

What is claimed is:

1. In a method for assaying an analyte comprising applying a liquid sample having a relatively high viscosity containing the analyte onto a spreading layer of a multilayer analysis element comprising a support having laminated thereon, in sequence, at least one reagent layer containing a substance capable of converting a detectable chemical species upon reaction with said analyte and a liquid sample-spreading layer and then detecting said detectable chemical species, the improvement which comprises applying a wetting liquid onto said spreading layer of the multilayer analysis element prior to applying said liquid sample to the multilayer analysis element, said liquid sample being applied to the multilayer analysis element while at least the surface of said spreading layer is maintained wet with said wetting liquid.

2. The method of claim 1 wherein said wetting liquid comprises (1) water, (2) glycerin, (3) an alcohol, (4) a polar solvent other than water or (5) a mixture of glycerin, an alcohol or a polar solvent with water.

3. The method of claim 2 wherein said alcohol is methanol, ethanol or propanol.

4. The method of claim 2 wherein said polar solvent is acetone or tetrahydrofuran.

5. The method of claim 2 wherein said mixture is a mixture of glycerin and water.

6. The method of claim 2 wherein the mixing ratio of (2), (3) or (4) with water is at least 0.1 vol%, based on 100 vol% of water.

7. The method of claim 2 wherein said wetting liquid is contained in an amount of about 0.1 to about 20 μl per 1 cm$^2$ of said spreading layer.

8. The method of claim 7 wherein said wetting liquid contains a water-soluble additive.

9. The method of claim 8 wherein said additive is selected from the group consisting of an organic or inorganic salt, a surface active agent, a buffer, an organic or inorganic alkali, an acid, a high molecular weight substance and an oxidation-reduction substance.

10. The method of claim 9 wherein said organic or inorganic salt is selected from the group consisting of sodium chloride, a phosphate and calcium chloride.

11. The method of claim 9 wherein said surface active agent is an anionic suface active agent, a cationic surface active agent or a nonionic surface active agent.

12. The method of claim 9 wherein said buffer is selected from the group consisting of a $Na_2HPO_4$—$KH_2PO_4$ buffer solution, a $Na_2HPO_4$—citric acid buffer solution and a tris(hydroxymethyl)aminomethane-hydrochloride buffer solution.

13. The method of claim 9 wherein said high molecular weight substance is protein.

14. The method of claim 13 wherein said protein is albumin.

15. The method of claim 9 wherein said organic or inorganic acid is selected from the group consisting of citric acid, acetic acid, phosphoric acid, hydrochloric acid and tartaric acid.

16. The method of claim 9 wherein said organic or inorganic alkali is selected from the group consisting of sodium hydroxide, sodium carbonate, sodium bicarbonate, ammonia and triethylamine.

17. The method of claim 9 wherein said oxidation-reduction substance is ascorbic acid.

18. The method of claim 1, wherein said wetting liquid is contained in an amount of at least 0.1 μl per 1 cm$^2$ of the spreading layer.

19. The method of claim 18, wherein said wetting liquid is contained in an amount of 0.1 to 20 μl per 1 cm$^2$ of the spreading layer.

20. The method of claim 19, wherein said wetting liquid is contained in an amount of 0.5 to 20 μl per 1 cm$^2$ of the spreading layer.

21. The method of claim 1, wherein said liquid sample has a viscosity of about 20 to 50 cps, measured at 25° C.

22. The method of claim 1, wherein said liquid sample is applied to the spreading layer within 30 seconds after application of wetting liquid.

23. The method of claim 5 wherein the mixing ratio of glycerin with water is at least 0.1 vol%, based on 100 vol% of water.

* * * * *